United States Patent
Huo et al.

(10) Patent No.: US 9,150,472 B2
(45) Date of Patent: Oct. 6, 2015

(54) METHOD AND COMPOSITION FOR INHIBITING ASPHALTENE DEPOSITION IN A HYDROCARBON MIXTURE

(71) Applicants: Zhongxin Huo, Katy, TX (US); Timothy Michael Shea, The Woodlands, TX (US); Cornelis Antonius Theodorus Kuijvenhoven, Rijswijk (NL); Ying Zhang, Sugar Land, TX (US)

(72) Inventors: Zhongxin Huo, Katy, TX (US); Timothy Michael Shea, The Woodlands, TX (US); Cornelis Antonius Theodorus Kuijvenhoven, Rijswijk (NL); Ying Zhang, Sugar Land, TX (US)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 14/366,828

(22) PCT Filed: Dec. 17, 2012

(86) PCT No.: PCT/US2012/070141
§ 371 (c)(1),
(2) Date: Jun. 19, 2014

(87) PCT Pub. No.: WO2013/096218
PCT Pub. Date: Jun. 27, 2013

(65) Prior Publication Data
US 2014/0350299 A1    Nov. 27, 2014

Related U.S. Application Data

(60) Provisional application No. 61/578,292, filed on Dec. 21, 2011.

(51) Int. Cl.
*C10G 75/04* (2006.01)
*C07C 7/20* (2006.01)
*C09K 8/524* (2006.01)
*E21B 43/25* (2006.01)

(52) U.S. Cl.
CPC . *C07C 7/20* (2013.01); *C09K 8/524* (2013.01); *C10G 75/04* (2013.01); *E21B 43/25* (2013.01)

(58) Field of Classification Search
CPC .......... C07C 7/20; E21B 43/35; C09K 8/524; C10G 75/04
USPC .............................................. 562/571; 585/4
See application file for complete search history.

(56) References Cited

U.S. PATENT DOCUMENTS

| | | |
|---|---|---|
| 3,275,554 A | 9/1966 | Wagenaar |
| 3,438,757 A | 4/1969 | Honnen et al. |
| 3,565,804 A | 2/1971 | Honnen et al. |
| 3,755,433 A | 8/1973 | Miller et al. |
| 3,822,209 A | 7/1974 | Knapp et al. |
| 3,996,059 A | 12/1976 | Stansfield et al. |
| 4,224,212 A | 9/1980 | Topham |
| 4,349,389 A | 9/1982 | Schofield |
| 4,882,034 A | 11/1989 | Tack et al. |
| 5,000,792 A | 3/1991 | Ohta et al. |
| 5,425,422 A | 6/1995 | Jamaluddin et al. |
| 5,536,445 A | 7/1996 | Campbell et al. |
| 5,646,212 A | 7/1997 | Hibbert |
| 5,753,022 A | 5/1998 | Schofield et al. |
| 5,833,721 A | 11/1998 | Hart et al. |
| 5,855,629 A | 1/1999 | Grundy et al. |
| 5,858,927 A | 1/1999 | Poelker et al. |
| 6,444,784 B1 | 9/2002 | Patil et al. |
| 7,008,988 B2 * | 3/2006 | Thetford et al. ............ 524/322 |
| 7,097,759 B2 | 8/2006 | Mukkamala |
| 7,795,183 B2 | 9/2010 | Wilkes et al. |
| 2002/0033265 A1 | 3/2002 | Varadaraj |
| 2007/0042911 A1 | 2/2007 | Fletcher |
| 2010/0084597 A1 | 4/2010 | Schwab et al. |
| 2011/0092393 A1 | 4/2011 | Faust et al. |
| 2011/0203353 A1 * | 8/2011 | Hough et al. ................ 73/61.62 |
| 2011/0207640 A1 | 8/2011 | Carty et al. |

FOREIGN PATENT DOCUMENTS

| | | | |
|---|---|---|---|
| EP | 0164817 A2 | | 12/1985 |
| GB | 1342746 | | 1/1974 |
| GB | 1373660 | | 11/1974 |
| GB | 2337522 | * | 11/1999 |
| WO | WO 00/24503 | * | 5/2000 |
| WO | WO 02/077111 | * | 10/2002 |
| WO | 2005100517 A1 | | 10/2005 |
| WO | 2006111712 A2 | | 10/2006 |
| WO | 2010014678 A1 | | 2/2010 |
| WO | 2010015706 A1 | | 2/2010 |

OTHER PUBLICATIONS

PCT International Search Report, Application No. PCT/US2012/070141 dated Apr. 5, 2013.
Morao, A. etal. 'Effect of antifoam addition on gas-liquid mass transfer in stirred fermenters.' Bioprocess Engineering, 1999, vol. 20, pp. 165-172.
Predel, T. et al. 'Ionic Liquids as Alternative Lubricants for Special Applications.' Chemical Engineering & Technology, 2010, vol. 33, No. 1, pp. 132-136.
Jose-Alberto, M. et al. 'Current Knowledge and Potential Applications of Ionic Liquids in the Petroleum Industry' Ionic Liquides : Applications and Perspectives. Feb. 21, 2011, Chapter 18, pp. 439-458.

* cited by examiner

*Primary Examiner* — Shailendra Kumar

(57) ABSTRACT

A method of inhibiting the deposition of asphaltene in a mixture comprising hydrocarbons, the method comprising contacting the mixture with a composition which comprises at least one poly(hydroxycarboxylic acid) amide salt derivative.

7 Claims, No Drawings

METHOD AND COMPOSITION FOR INHIBITING ASPHALTENE DEPOSITION IN A HYDROCARBON MIXTURE

PRIORITY CLAIM

The present application is a National Stage (§371) application of PCT/US2012/070141, filed Dec. 17, 2012, which claims priority from U.S. Provisional Application 61/578,292, filed Dec. 21, 2011, each of which are hereby incorporated by reference in their entirety.

FIELD OF THE INVENTION

The invention relates to methods and compositions for inhibiting the deposition of asphaltenes in a hydrocarbon mixture and in one embodiment to methods and compositions for inhibiting the deposition of asphaltenes during the production of oil and gas.

BACKGROUND

Crude oil produced from production wells often contains asphaltenes that form deposits that can cause plugging of production equipment and plugging of the near wellbore formation. It can be very difficult to remove these asphaltenes and to recover from a plugged formation. Asphaltenes are the heaviest and most polar components in crude oil and they often contain nitrogen, oxygen, sulfur and trace amounts of vanadium and nickel. Heavier oils contain much higher proportions of asphaltenes.

When the crude oil is produced from a well, asphaltenes begin to deposit out of the hydrocarbon and can plug the pipe or the formation.

SUMMARY OF THE INVENTION

This invention provides a method of inhibiting the deposition of asphaltenes in a mixture comprising hydrocarbons, the method comprising contacting the mixture with a composition which comprises at least one poly(hydroxycarboxylic acid) amide salt derivative.

This invention further provides a composition for inhibiting the deposition of asphaltenes in a hydrocarbon mixture which comprises at least one poly(hydroxycarboxylic acid) amide salt derivative.

This invention also provides an asphaltene inhibited mixture comprising water, hydrocarbons, and a composition comprising at least one poly(hydroxycarboxylic acid) amide salt derivative.

DETAILED DESCRIPTION OF THE INVENTION

The present invention is directed to a method of treating hydrocarbons produced from oil and gas production wells. These hydrocarbons are prone to depositing asphaltenes during the production, transport and processing steps which these hydrocarbons undergo. The present invention addresses this problem by treating the hydrocarbons with a composition comprising one or more ionic liquids. The ionic liquid(s) may be combined with additional components known to those of ordinary skill in the art that are useful for treating hydrocarbons produced from hydrocarbon production wells.

Ionic liquids are generally defined as molten salts which are liquid at room temperature or by definition have a melting point of less than 100° C. They have virtually no vapor pressure and can exhibit high thermal stability. As the term ionic liquids is used in this application, it may apply to the above described molten salts or to the salts dissolved in solution, aqueous or otherwise.

An ionic liquid can be presented by the formula $C^+A^-$ wherein $C^+$ is a suitable cation and $A^-$ is a suitable anion.

A preferred embodiment of an ionic liquid is a poly(hydroxycarboxylic acid) amide salt derivative. The poly(hydroxycarboxylic acid) amide salt derivative(s) may be combined with additional components known to those of ordinary skill in the art that are useful for treating hydrocarbons produced from hydrocarbon production wells.

The poly(hydroxycarboxylic acid) amide salt derivatives used in the present invention may also be referred to as hyperdispersants. The one or more poly(hydroxycarboxylic acid) amide salt derivatives of the present invention are poly(hydroxycarboxylic acid) amide salt derivatives having formula (III):

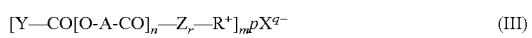

$$[Y\text{—}CO[O\text{-}A\text{-}CO]_n\text{—}Z_r\text{—}R^+]_m pX^{q-} \qquad (III)$$

wherein Y is hydrogen or optionally substituted hydrocarbyl group, A is a divalent optionally substituted hydrocarbyl group, n is from 1 to 100, m is from 1 to 4, q is from 1 to 4 and p is an integer such that pq=m, Z is an optionally substituted divalent bridging group which is attached to the carbonyl group through a nitrogen atom, r is 0 or 1, $R^+$ is an ammonium group and $X^{q-}$ is an anion.

$R^+$ may be a primary, secondary, tertiary or quaternary ammonium group. $R^+$ is preferably a quaternary ammonium group.

In formula (III), A is preferably a divalent straight chain or branched hydrocarbyl group as hereafter described for formulas (I) and (II) below.

That is to say, in formula (III), A is preferably an optionally substituted aromatic, aliphatic or cycloaliphatic straight chain or branched divalent hydrocarbyl group. More preferably, A is an arylene, alkylene or alkenylene group, in particular an arylene, alkylene or alkenylene group containing in the range of from 4 to 25 carbon atoms, more preferably in the range of from 6 to 25 carbon atoms, more preferably in the range of from 8 to 24 carbon atoms, more preferably in the range of from 10 to 22 carbon atoms, and most preferably in the range of from 12 to 20 carbon atoms.

Preferably, in said compound of formula (III), there are at least 4 carbon atoms, more preferably at least 6 carbon atoms, and even more preferably in the range of from 8 to 14 carbon atoms connected directly between the carbonyl group and the oxygen atom derived from the hydroxyl group.

In the compound of formula (III), the optional substituents in the group A are preferably selected from hydroxy, halo or alkoxy groups, especially $C_{1-4}$ alkoxy groups.

In formula (III) (and formula (I)), n is in the range of from 1 to 100. Preferably, the lower limit of the range for n is 1, more preferably 2, even more preferably 3; preferably the upper limit of the range for n is 100, more preferably 60, more preferably 40, more preferably 20, and even more preferably 10 (i.e. n may be selected from any of the following ranges: from 1 to 100; from 2 to 100; from 3 to 100; from 1 to 60; from 2 to 60; from 3 to 60; from 1 to 40; from 2 to 40; from 3 to 40; from 1 to 20; from 2 to 20; from 3 to 20; from 1 to 10; from 2 to 10; and, from 3 to 10).

In formula (III), Y is preferably an optionally substituted hydrocarbyl group as hereinafter described for formula (I).

That is to say, the optionally substituted hydrocarbyl group Y in formula (III) is preferably aryl, alkyl or alkenyl containing up to 50 carbon atoms, more preferably in the range of from 7 to 25 carbon atoms. For example, the optionally substituted hydrocarbyl group Y may be conveniently selected from heptyl, octyl, undecyl, lauryl, heptadecyl, heptadenyl, heptadecadienyl, stearyl, oleyl and linoleyl.

Other examples of said optionally substituted hydrocarbyl group Y in formula (III) herein include $C_{4-8}$ cycloalkyls such as cyclohexyl; polycycloalkyls such as polycyclic terpenyl groups which are derived from naturally occurring acids such as abietic acid; aryls such as phenyl; aralkyls such as benzyl; and polyaryls such as naphthyl, biphenyl, stibenyl and phenylmethylphenyl.

In the present invention, the optionally substituted hydrocarbyl group Y in formula (III) may contain one or more functional groups such as carbonyl, carboxyl, nitro, hydroxy, halo, alkoxy, amino, preferably tertiary amino (no N—H linkages), oxy, cyano, sulphonyl and sulphoxyl. The majority of the atoms, other than hydrogen, in substituted hydrocarbyl groups are generally carbon, with the heteroatoms (e.g., oxygen, nitrogen and sulfur) generally representing only a minority, about 33% or less, of the total non-hydrogen atoms present.

Those skilled in the art will appreciate that functional groups such as hydroxy, halo, alkoxy, nitro and cyano in a substituted hydrocarbyl group Y will displace one of the hydrogen atoms of the hydrocarbyl, whilst functional groups such as carbonyl, carboxyl, tertiary amino (—N—), oxy, sulphonyl and sulphoxyl in a substituted hydrocarbyl group will displace a —CH— or —CH$_2$— moiety of the hydrocarbyl.

More preferably, the hydrocarbyl group Y in formula (III) is unsubstituted or substituted by a group selected from hydroxy, halo or alkoxy group, even more preferably $C_{1-4}$ alkoxy.

Most preferably, the optionally substituted hydrocarbyl group Y in formula (III) is a stearyl group, 12-hydroxystearyl group, an oleyl group or a 12-hydroxyoleyl group, and that derived from naturally occurring oil such as tall oil fatty acid.

In formula (III), Z is preferably an optionally substituted divalent bridging group represented by formula (IV)

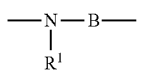

(IV)

wherein $R^1$ is hydrogen or a hydrocarbyl group and B is an optionally substituted alkylene group.

Examples of hydrocarbyl groups that may represent $R^1$ include methyl, ethyl, n-propyl, n-butyl and octadecyl. Examples of optionally substituted alkylene groups that may represent B include ethylene, trimethylene, tetramethylene and hexamethylene. Examples of preferred Z moieties in formula (III) include —NHCH$_2$CH$_2$—, —NHCH$_2$C(CH$_3$)$_2$CH$_2$— and —NH(CH$_2$)$_3$—.

In formula (III), r is preferably 1, i.e. the poly(hydroxycarboxylic acid) amide salt derivative having formula (III) must contain the optionally substituted divalent bridging group Z.

Preferably, $R^+$ may be represented by formula (V)

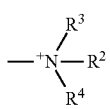

(V)

wherein $R^2$, $R^3$ and $R^4$ may be selected from hydrogen and alkyl groups such as methyl.

The anion $X^{q-}$ of the compound of formula (III) is not critical and can be any anion (or mixture of anions) suitable to balance the positive charge of the poly(hydroxycarboxylic acid) amide cation.

The anion $X^{q-}$ of the compound of formula (III) may conveniently be a sulfur-containing anion, such as an anion selected from sulfate and sulfonate anions.

However, it may be desirable to maintain a low sulfur content in the oil and gas being produced so the use of non-sulfur-containing anions in the compounds of formula (III) may be desirable depending upon the concentration of sulfur in the oil and gas and/or the desired concentration of sulfur in the oil and gas composition containing the one or more poly(hydroxycarboxylic acid) amide salt derivatives.

Therefore, the anion $X^{q-}$ of the compound of formula (III) can also be any non-sulfur-containing anion (or mixture of anions) suitable to balance the positive charge of the poly(hydroxycarboxylic acid) amide cation, such as a non-sulfur-containing organic anion or a non-sulfur-containing inorganic anion.

Non-limiting examples of suitable anions are $OH^-$, $CH^-$, $NH_3^-$, $HCO_3^-$, $HCOO^-$, $CH_3COO^-$, $H^-$, $BO_3^{3-}$, $CO_3^{2-}$, $C_2H_3O_2^-$, $HCO^{2-}$, $C_2O_4^{2-}$, $HC_2O_4^-$, $NO_3^-$, $NO_2^-$, $N^{3-}$, $NH_2^-$, $O^{2-}$, $O_2^-$, $BeF_3^-$, $F^-$, $Na^-$, $[Al(H_2O)_2(OH)_4]^-$, $SiO_3^{2-}$, $SiF_6^{2-}$, $H_2PO_4^-$, $P^{3-}$, $PO_4^{3-}$, $HPO_4^{2-}$, $Cl^-$, $ClO_3^-$, $ClO_4^-$, $ClO^-$, $KO^-$, $SbOH_6^-$, $SnCl_6^{2-}$, $[SnTe4]^{4-}$, $CrO_4^{2-}$, $Cr_2O_7^{2-}$, $MnO_4^-$, $NiCl_6^{2-}$, $[Cu(CO_3)_2(OH)_2]^{4-}$, $AsO_4^{3-}$, $Br^-$, $BrO_3^-$, $IO_3^-$, $I^-$, $CN^-$, $OCN^-$, etc.

Suitable anions may also include anions derived from compounds containing a carboxylic acid group (e.g. a carboxylate anion), anions derived from compounds containing a hydroxyl group (e.g. an alkoxide, phenoxide or enolate anion), nitrogen based anions such as nitrate and nitrite, phosphorus based anions such as phosphates and phosphonates, or mixtures thereof.

Non-limiting examples of suitable anions derived from compounds containing a carboxylic acid group include acetate, oleate, salicylate anions, and mixtures thereof.

Non-limiting examples of suitable anions derived from compounds containing a hydroxyl group include phenate anions, and mixtures thereof.

In a preferred embodiment of the present invention, the anion $X^{q-}$ is a non-sulfur-containing anion selected from the group consisting of OH, a phenate group, a salicylate group, an oleate group and an acetate group; more preferably the anion $X^{q-}$ is OH.

The one or more poly(hydroxycarboxylic acid) amide salt derivatives may be obtained by reaction of an amine and a poly(hydroxycarboxylic acid) of formula (I)

$$Y—CO[O-A-CO]_n—OH \qquad (I)$$

wherein Y is hydrogen or optionally substituted hydrocarbyl group, A is a divalent optionally substituted hydrocarbyl group and n is from 1 to 100, with an acid or a quaternizing agent.

As used herein, the term "hydrocarbyl" represents a radical formed by removal of one or more hydrogen atoms from a carbon atom of a hydrocarbon (not necessarily the same carbon atoms in case more hydrogen atoms are removed).

Hydrocarbyl groups may be aromatic, aliphatic, acyclic or cyclic groups. Preferably, hydrocarbyl groups are aryl, cycloalkyl, alkyl or alkenyl, in which case they may be straight-chain or branched-chain groups.

Representative hydrocarbyl groups include phenyl, naphthyl, methyl, ethyl, butyl, pentyl, methylpentyl, hexenyl, dimethylhexyl, octenyl, cyclooctenyl, methylcyclooctenyl, dimethylcyclooctyl, ethylhexyl, octyl, isooctyl, dodecyl, hexadecenyl, eicosyl, hexacosyl, triacontyl and phenylethyl.

In the present invention, the phrase "optionally substituted hydrocarbyl" is used to describe hydrocarbyl groups optionally containing one or more "inert" heteroatom-containing functional groups. By "inert" is meant that the functional groups do not interfere to any substantial degree with the function of the compound.

The optionally substituted hydrocarbyl group Y in formula (I) herein is preferably aryl, alkyl or alkenyl containing up to 50 carbon atoms, more preferably in the range of from 7 to 25 carbon atoms. For example, the optionally substituted hydrocarbyl group Y may be conveniently selected from heptyl, octyl, undecyl, lauryl, heptadecyl, heptadenyl, heptadecadienyl, stearyl, oleyl and linoleyl.

Other examples of said optionally substituted hydrocarbyl group Y in formula (I) herein include $C_{4-8}$ cycloalkyls such as cyclohexyl; polycycloalkyls such as polycyclic terpenyl groups which are derived from naturally occurring acids such as abietic acid; aryls such as phenyl; aralkyls such as benzyl; and polyaryls such as naphthyl, biphenyl, stibenyl and phenylmethylphenyl.

In the present invention, the optionally substituted hydrocarbyl group Y may contain one or more functional groups such as carbonyl, carboxyl, nitro, hydroxy, halo, alkoxy, tertiary amino (no N—H linkages), oxy, cyano, sulphonyl and sulphoxyl. The majority of the atoms, other than hydrogen, in substituted hydrocarbyl groups are generally carbon, with the heteroatoms (e.g., oxygen, nitrogen and sulfur) generally representing only a minority, about 33% or less, of the total non-hydrogen atoms present.

Those skilled in the art will appreciate that functional groups such as hydroxy, halo, alkoxy, nitro and cyano in a substituted hydrocarbyl group Y will displace one of the hydrogen atoms of the hydrocarbyl, whilst functional groups such as carbonyl, carboxyl, tertiary amino (—N—), oxy, sulphonyl and sulphoxyl in a substituted hydrocarbyl group will displace a —CH— or —$CH_2$— moiety of the hydrocarbyl.

The hydrocarbyl group Y in formula (I) is more preferably unsubstituted or substituted by a group selected from hydroxy, halo or alkoxy group, even more preferably $C_{1-4}$ alkoxy.

Most preferably, the optionally substituted hydrocarbyl group Y in formula (I) is a stearyl group, 12-hydroxystearyl group, an oleyl group, a 12-hydroxyoleyl group or a group derived from naturally occurring oil such as tall oil fatty acid.

In one embodiment of the present invention, at least one of, or all of, the one or more poly(hydroxycarboxylic acid) amide salt derivatives are sulfur-containing poly(hydroxycarboxylic acid) amide salt derivatives.

In such an embodiment, said one or more poly(hydroxycarboxylic acid) amide salt derivatives preferably have a sulfur content of at most 2.5 wt. %, such as a sulfur content in the range of from 0.1 to 2.0 wt. %, conveniently in the range of from 0.6 to 1.2 wt. % sulfur, as measured by ICP-AES, based on the total weight of said poly(hydroxycarboxylic acid) amide salt derivatives.

In another embodiment of the present invention, the one or more poly(hydroxycarboxylic acid) amide salt derivatives are non-sulfur-containing poly(hydroxycarboxylic acid) amide salt derivatives.

The preparation of polyhydroxycarboxylic acid and its amide or other derivatives is known and is described, for instance, in EP 0164817, U.S. Pat. No. 5,753,022, U.S. Pat. No. 5,646,212, U.S. Pat. No. 5,536,445, U.S. Pat. No. 4,224,212, GB 1342746, GB 1373660, U.S. Pat. No. 5,000,792 and U.S. Pat. No. 4,349,389 which disclosures are herein incorporated by reference.

The polyhydroxycarboxylic acids of formula (I) may be made by the interesterification of one or more hydroxycarboxylic acids of formula (II)

HO-A-COOH  (II)

wherein A is a divalent optionally substituted hydrocarbyl group, optionally in the presence of a catalyst according to well known methods. Such methods are described, for example, in U.S. Pat. No. 3,996,059, GB 1373660 and GB 1342746.

The chain terminator in said interesterification may be a non-hydroxycarboxylic acid.

The hydroxyl group in the hydroxycarboxylic acid and the carboxylic acid group in the hydroxycarboxylic acid or the non-hydroxycarboxylic acid may be primary, secondary or tertiary in character.

The interesterification of the hydroxycarboxylic acid and the non-hydroxycarboxylic acid chain terminator may be effected by heating the starting materials, optionally in a suitable hydrocarbon solvent such as toluene or xylene, and azeotroping off the formed water. The reaction may be carried out at a temperature up to –250° C., conveniently at the reflux temperature of the solvent.

Where the hydroxyl group in the hydroxycarboxylic acid is secondary or tertiary, the temperature employed should not be so high as to lead to dehydration of the acid molecule.

Catalysts for the interesterification, such as p-toluenesulfonic acid, zinc acetate, zirconium naphthenate or tetrabutyl titanate, may be included, with the objective of either increasing the rate of reaction at a given temperature or of reducing the temperature required for a given rate of reaction.

In the compounds of formula (I) and (II), A is preferably an optionally substituted aromatic, aliphatic or cycloaliphatic straight chain or branched divalent hydrocarbyl group. Preferably, A is an arylene, alkylene or alkenylene group, in particular an arylene, alkylene or alkenylene group containing in the range of from 4 to 25 carbon atoms, more preferably in the range of from 6 to 25 carbon atoms, more preferably in the range of from 8 to 24 carbon atoms, more preferably in the range of from 10 to 22 carbon atoms, and most preferably in the range of from 12 to 20 carbon atoms.

Preferably, in said compounds of formula (I) and (II), there are at least 4 carbon atoms, more preferably at least 6 carbon atoms, and even more preferably in the range of from 8 to 14 carbon atoms connected directly between the carbonyl group and the oxygen atom derived from the hydroxyl group.

In the compounds of formula (I) and (II), the optional substituents in the group A are preferably selected from hydroxy, halo or alkoxy groups, more preferably $C_{1-4}$ alkoxy groups.

The hydroxyl group in the hydroxycarboxylic acids of formula (II) is preferably a secondary hydroxyl group.

Examples of suitable hydroxycarboxylic acids are 9-hydroxystearic acid, 10-hydroxystearic acid, 12-hydroxystearic acid, 12-hydroxy-9-oleic acid (ricinoleic acid), 6-hydroxycaproic acid, preferably 12-hydroxystearic acid. Commercial 12-hydroxystearic acid (hydrogenated castor oil fatty acid) normally contains up to 15% wt of stearic acid and other non-hydroxycarboxylic acids as impurities and can conveniently be used without further admixture to produce a polymer of molecular weight about 1000-2000.

Where the non-hydroxycarboxylic acid is introduced separately to the reaction, the proportion which is required in order to produce a polymer or oligomer of a given molecular weight can be determined either by simple experiment or by calculation by the person skilled in the art.

The group (—O-A-CO—) in the compounds of formula (I) and (II) is preferably a 12-oxystearyl group, 12-oxyoleyl group or a 6-oxycaproyl group.

Preferred polyhydroxycarboxylic acids of formula (I) for reaction with amine include poly(hydroxystearic acid) and poly(hydroxyoleic acid).

The amines which react with polyhydroxycarboxylic acids of formula (I) to form poly(hydroxycarboxylic acid) amide intermediates may include those defined in U.S. Pat. No. 5,855,629.

For example, various amines and their preparations are described in U.S. Pat. No. 3,275,554, U.S. Pat. No. 3,438,757, U.S. Pat. No. 3,454,555, U.S. Pat. No. 3,565,804, U.S. Pat. No. 3,755,433 and U.S. Pat. No. 3,822,209 which disclosures are herein incorporated by reference.

The amine reactant is preferably a diamine, a triamine or a polyamine. Preferred amine reactants are diamines selected from ethylenediamine, N,N-dimethyl-1,3-propanediamine, triamines and polyamines selected from dietheylenetriamine, triethylenetetramine, tetraethylenepentamine, pentaethylenehexamine and tris(2-aminoethyl)amine.

The amidation between the amine reactant and the poly(hydroxycarboxylic acid) of formula (I) may be carried out according to methods known to those skilled in the art, by heating the poly(hydroxycarboxylic acid) with the amine reactant, optionally in a suitable hydrocarbon solvent such as toluene or xylene, and azeotroping off the formed water. Said reaction may be carried out in the presence of a catalyst such as p-toluenesulfonic acid, zinc acetate, zirconium naphthenate or tetrabutyl titanate.

The poly(hydroxycarboxylic acid) amide intermediate formed from reaction of the amine and the poly(hydroxycarboxylic acid) of formula (I) is reacted with an acid or a quaternizing agent to form a salt derivative, according to well-known methods.

Acids that may be used to form the salt derivative may be selected from organic or inorganic acids. Said acids are conveniently selected from carboxylic acids, nitrogen-containing organic and inorganic acids, sulfur-containing organic or inorganic acids (such as sulfuric acid, methanesulfonic acid and benzenesulfonic acid).

Quaternizing agents that may be used to form the salt derivative may be selected from dimethylsulfuric acid, a dialkyl sulfate having from 1 to 4 carbon atoms, an alkyl halide such as methyl chloride, methyl bromide, aryl halide such as benzyl chloride.

In a preferred embodiment, the quaternizing agent is a sulfur-containing quaternizing agent, in particular dimethylsulfuric acid or an dialkyl sulfate having from 1 to 4 carbon atoms. The quaternizing agent is preferably dimethyl sulfate.

Quaternization is a well-known method in the art. For example, quaternization using dimethyl sulfate is described in U.S. Pat. No. 3,996,059, U.S. Pat. No. 4,349,389 and GB 1373660.

Poly(hydroxycarboxylic acid) amide salt derivatives that are preferred in the present invention are those which each have a TBN (total base number) value of less than 10 mg KOH/g, as measured by ASTM D 4739. More preferably, the poly(hydroxycarboxylic acid) amide salt derivatives each have a TBN value of less than 5 mg KOH/g, most preferably 2 mg KOH/g or less, as measured by ASTM D 4739.

The ionic liquid comprising treatment fluid may be injected into a production well, into an injection well, into the hydrocarbon production system or in any other manner known to one of ordinary skill in the art. The treatment fluid may be injected at one or more locations and more than one different treatment fluid may be injected together or separately in different locations or at different times.

It is believed that the composition comprising ionic liquids is effective at reducing the asphaltene deposition in the near wellbore region of the formation because the ionic liquids are polar and can absorb and/or adhere to the rock of the formation. To achieve this effect, the ionic liquids must be injected through an injection well into the near wellbore region of a hydrocarbon containing formation This allows the ionic liquids to continue to inhibit asphaltene deposition for much longer than any typical chemicals injected into the well that are immediately pumped back out with the hydrocarbon.

The method of the present invention reduces or inhibits the deposition of asphaltenes as shown in the following illustrative examples.

EXAMPLES

Example 1 compares the impact on asphaltene deposition of an ionic liquid. In this experiment, a crude oil sample was placed into a test tube. Hexadecane was added until asphaltene particles began to deposit out of the oil. In a second experiment, a sample of the same oil was placed in a second test tube and 1000 ppmw of a poly(hydroxycarboxylic acid) amide salt derivative was added to the tube. Hexadecane was added to this test tube, too.

The P value was calculated according to the following formula $P=1+(\text{Volume of Heptane})/(\text{Mass of oil})$ for each experiment and is shown in Table 1. A higher P-value indicates that the asphaltene is more stable and less likely to deposit from the oil. As can be seen from the results, the addition of the poly(hydroxycarboxylic acid) amide salt derivative provides a composition where the asphaltene is more stable and less likely to deposit from the oil. Thus, the addition of the poly(hydroxycarboxylic acid) amide salt derivative reduces the likelihood of plugging caused by asphaltene deposition.

TABLE 1

| Test | P value |
|---|---|
| 1 | 1.25 |
| 2 | 2.5 |

The invention claimed is:

1. A method of inhibiting the deposition of asphaltene in a mixture comprising hydrocarbons, the method comprising contacting the mixture with a composition which comprises at least one poly(hydroxycarboxylic acid) amide salt derivative having the chemical formula $[Y-CO[O-A-CO]_n-Z_r-R^+]_m pX^{q-}$, wherein Y is hydrogen or optionally substituted hydrocarbyl group, A is a divalent optionally substituted hydrocarbyl group, n is from 1 to 100, m is from 1 to 4, q is from 1 to 4 and p is an integer such that pq=m, Z is an optionally substituted divalent bridging group which is attached to the carbonyl group through a nitrogen atom, r is 0 or 1, $R^+$ is an ammonium group and $X^{q-}$ is an anion.

2. The method of claim 1 wherein the poly(hydroxycarboxylic acid) amide salt derivative is injected into the well head or an injection well.

3. The method of claim 1 wherein the poly(hydroxycarboxylic acid) amide salt derivative is injected into the pipeline transporting the crude oil.

4. The method of claim 1 wherein the poly(hydroxycarboxylic acid) amide salt derivative is injected into the near wellbore region of a hydrocarbon containing formation.

5. A composition for inhibiting the deposition of asphaltenes in a hydrocarbon mixture which comprises at least one poly(hydroxycarboxylic acid) amide salt derivative having the chemical formula $[Y-CO[O-A-CO]_n-Z_r-R^+]_m pX^{q-}$, wherein Y is hydrogen or optionally substituted hydrocarbyl group, A is a divalent optionally substituted hydrocarbyl group, n is from 1 to 100, m is from 1 to 4, q is from 1 to 4 and p is an integer such that pq=m, Z is an optionally substituted divalent bridging group which is attached to the carbonyl group through a nitrogen atom, r is 0 or 1, $R^+$ is an ammonium group and $X^{q-}$ is an anion.

6. An asphaltene inhibited mixture comprising hydrocarbons and a composition comprising at least one poly(hydroxycarboxylic acid) amide salt derivative having the chemical formula $[Y-CO[O-A-CO]_n-Z_r-R^+]_m pX^{q-}$, wherein Y is hydrogen or optionally substituted hydrocarbyl group, A is a divalent optionally substituted hydrocarbyl group, n is from 1 to 100, m is from 1 to 4, q is from 1 to 4 and p is an integer such that pq=m, Z is an optionally substituted divalent bridging group which is attached to the carbonyl group through a nitrogen atom, r is 0 or 1, $R^+$ is an ammonium group and $X^{q-}$ is an anion.

7. The mixture of claim 6 wherein the hydrocarbons comprise crude oil produced from a hydrocarbon containing formation.

\* \* \* \* \*